(12) United States Patent
Aouissi et al.

(10) Patent No.: US 10,865,175 B1
(45) Date of Patent: Dec. 15, 2020

(54) METHOD OF SYNTHESIZING CYCLOHEXANONE

(71) Applicant: KING SAUD UNIVERSITY, Riyadh (SA)

(72) Inventors: Ahmed Mohammed Aouissi, Riyadh (SA); Zeid Abdullah ALOthman, Riyadh (SA); Abdullah Ali Sultan Al-Kahtani, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/894,830

(22) Filed: Jun. 7, 2020

(51) Int. Cl.

| | |
|---|---|
| *C07C 45/78* | (2006.01) |
| *C08F 220/08* | (2006.01) |
| *C08F 212/08* | (2006.01) |
| *C08F 234/02* | (2006.01) |
| *C08J 5/18* | (2006.01) |
| *B01D 67/00* | (2006.01) |
| *B01D 71/80* | (2006.01) |
| *B01D 61/36* | (2006.01) |

(52) U.S. Cl.
CPC .......... *C07C 45/786* (2013.01); *B01D 61/362* (2013.01); *B01D 67/0006* (2013.01); *B01D 71/80* (2013.01); *C08F 212/08* (2013.01); *C08F 220/08* (2013.01); *C08F 234/02* (2013.01); *C08J 5/18* (2013.01); *C08J 2325/14* (2013.01); *C08J 2333/06* (2013.01); *C08J 2345/00* (2013.01)

(58) Field of Classification Search
CPC .... C07C 45/786; C08F 220/08; C08F 212/08; C08F 234/02; C08J 5/18; B01D 67/00
See application file for complete search history.

(56) References Cited

U.S. PATENT DOCUMENTS 4,532,347 A    7/1985    Vaughan

FOREIGN PATENT DOCUMENTS

| CN | 204051046 | 12/2014 |
| CN | 105457329 | 4/2016 |

OTHER PUBLICATIONS

Okushita et al. Journal of Membrane Science, (1995), 105, p. 51-53. (disclosed in IDS).*
Okushita et al., "Pervaporation of cyclohexane/cyclohexanone/cyclohexanol mixture through polyoxyethylene grafting nylon 6 membrane," Journal of Membrane Science, vol. 105, Issues 1-2, Sep. 15, 1995, pp. 51-53.
Okushita et al., "Synthesis of polyoxyethylene grafting nylon 6 and the selective separation of cyclohexane/cyclohexanone/cyclohexanol mixture through its membranes," Journal of Membrane Science, vol. 112, Issue 1, Apr. 3, 1996, pp. 91-100.
Peipei et al., "Pervaporation separation of cyclohexanol (cyclohexanone)/cyclohexane mixture by polyvinyl alcohol (PVA)/silica(SiO2) hybrid membrane," Chemical Industry and Engineering Progress, 33, 2014, 2693-2699.

* cited by examiner

*Primary Examiner* — Yong L Chu
(74) *Attorney, Agent, or Firm* — Nath, Goldberg & Meyer; Richard C. Litman

(57) ABSTRACT

A method of synthesizing cyclohexanone can include oxidation of cyclohexane to produce a mixture including cyclohexanone, cyclohexanol, and cyclohexane, and separating cyclohexanone from the mixture using a pervaporation method. The pervaporation method includes contacting the mixture with a first side of a poly(styrene-maleic anhydride-dihydropyrane) membrane and receiving the cyclohexanone from a second side of the poly(styrene-maleic anhydride-dihydropyrane) membrane as a low-pressure vapor. The method can be performed in a pervaporation unit including a reactant portion for receiving the cyclohexane, a permeate portion for receiving the cyclohexanone, and a poly(styrene-maleic anhydride-dihydropyrane) membrane separating the reactant portion from the permeate portion.

12 Claims, 2 Drawing Sheets

METHOD OF SYNTHESIZING CYCLOHEXANONE

BACKGROUND

1. Field

The disclosure of the present patent application relates to cyclohexanone synthesis, and particularly, to a method of synthesizing cyclohexanone using a pervaporation technique.

2. Description of the Related Art

Currently cyclohexanone is synthesized by oxidation of cyclohexane, leading to the formation of a mixture including cyclohexanone, cyclohexanol, and cyclohexane (FIG. 2). The cyclohexane conversion is kept very low (3-8%) with a selectivity of the cyclohexanone/cyclohexanol mixture (K/A) ranging between 70% and 80%. Also, conversion of cyclohexane is maintained at low levels (3%-8%) because increasing the conversion above these levels with conventional synthesis methods can lead to a decrease of cyclohexanone selectivity by further oxidation into other products, such as adipic acid, glutaric acid, succinic acid, oxalic acid, 2-hydroxy cyclohexanone, 1,2-cyclohexanedione and 2-cyclohexen-1-one. In other words, increased conversion using conventional synthesis methods can generate a great deal of by products and waste.

Thus, an enhanced method for synthesizing cyclohexanone solving the aforementioned problems are desired.

SUMMARY

A method of cyclohexanone synthesis can include oxidizing cyclohexane to obtain a mixture including cyclohexanone, cyclohexanol, and cyclohexane, and separating the cyclohexanone from the mixture by pervaporation using a poly(styrene-maleic anhydride-dihydropyrane) pervaporation membrane. The poly(styrene-maleic anhydride-dihydropyrane) pervaporation membrane can be synthesized by cationic polymerization of a mixture of styrene, maleic, and dihydropyrane monomers. The cyclohexanone can be extracted selectively and immediately through the pervaporation membrane. The method yields high quantities of cyclohexanone in an environmentally-friendly process. In addition, the cyclohexanone obtained has a high degree of purity. High purity of cyclohexanone is desirable when using cyclohexanone for other synthesis reactions, such as, polymerization of caprolactam.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
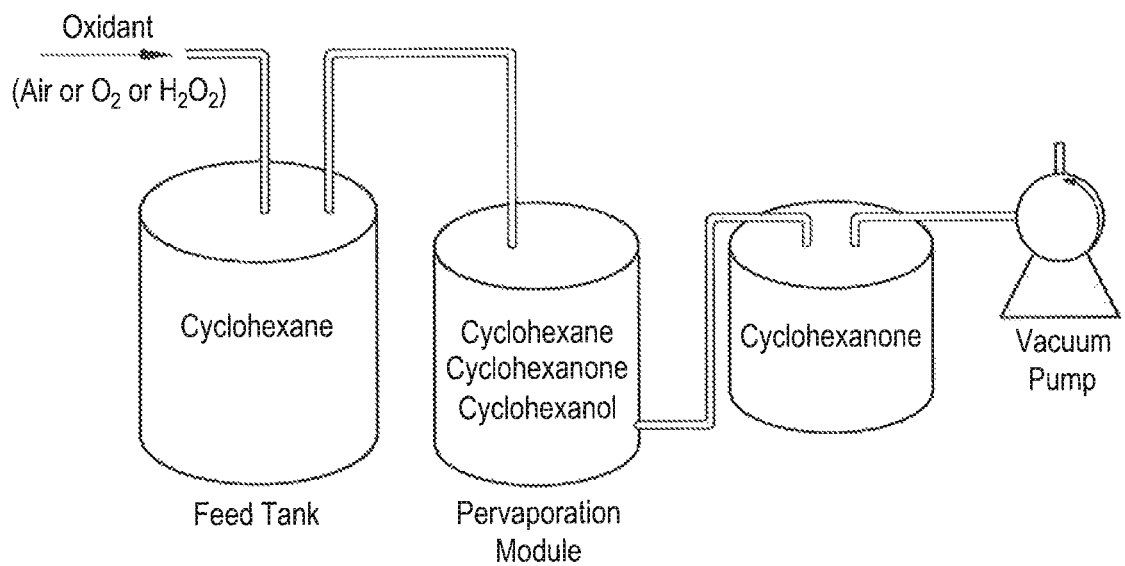
FIG. 1 depicts a schematic showing the pervaporation process for separating cyclohexanone from a cyclohexane/cyclohexanone/cyclohexanol mixture.
Figure 2:
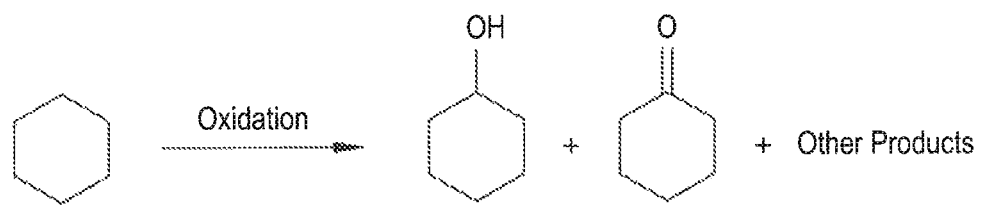
FIG. 2 depicts a reaction scheme for oxidation of cyclohexane into a cyclohexanol and cyclohexanone mixture.

A method of synthesizing cyclohexanone can include oxidation of cyclohexane to produce a mixture including cyclohexanone, cyclohexanol, and cyclohexane, and separating cyclohexanone from the mixture by a pervaporation method. The method can be performed in a pervaporation cell including a reactant portion for receiving the cyclohexane, a permeate portion for receiving the cyclohexanone, and a poly(styrene-maleic anhydride-dihydropyrane) membrane for separating the reactant portion from the permeate portion. Oxidation of the cyclohexane to produce the mixture can occur in the reactant portion. The pervaporation method includes contacting the mixture with a first side of the poly(styrene-maleic anhydride-dihydropyrane) membrane and receiving the cyclohexanone from a second side of the poly(styrene-maleic anhydride-dihydropyrane) membrane as a low-pressure vapor. The pervaporation membrane can be supported on a suitable horizontal support, e.g., a porous sintered stainless steel disk, positioned in the pervaporation cell.

The poly(styrene-maleic anhydride-dihydropyrane) pervaporation membrane can be synthesized by cationic polymerization of a mixture of styrene, maleic, and dihydropyrane monomers. The membrane can be used to separate cyclohexanone from the mixture of cyclohexane, cyclohexanone, and cyclohexane selectively and immediately through the pervaporation membrane.

According to an embodiment, the poly(styrene-maleic anhydride-dihydropyrane) pervaporation membrane can be used to separate cyclohexanone from a mixture including cyclohexanone. In an embodiment, the mixture can include cyclohexane, cyclohexanone, and cyclohexanol. In an embodiment, the separation can occur after oxidation of cyclohexane to separate cyclohexanone from the resulting cyclohexane-cyclohexanone-cyclohexanol mixture. In an embodiment, the mixture can include a 3:1:1 cyclohexane:cyclohexanone:cyclohexanol ratio. In an embodiment, the mixture can include cyclohexanone and cyclohexanol. In an embodiment, the separation can occur after oxidation of cyclohexanol to separate cyclohexanone from the resulting cyclohexanone-cyclohexanol mixture.

Throughout this application, the term "about" may be used to indicate that a value includes the standard deviation of error for the composition, device or method being employed to determine the value.

The use of the term "or" in the specification and claim(s) is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. In certain cases, the term "comprising" may be replaced with "consisting essentially of" or "consisting of."

The use of the word "a" or "an" when used herein in conjunction with the term "comprising" in the claims and/or the specification may mean "one," but it is also consistent with the meaning of "one or more," "at least one," and "one or more than one."

The membrane can be synthesized by dissolving maleic anhydride in acetone to form a first mixture, then adding styrene to the first mixture to form a second mixture. Then, 2,3-dihydro-4H-pyran can be added to the second mixture to form a third mixture. The third mixture can be mixed to homogeneity by heating. A suitable catalyst, such as $H_3PW_{12}O_{40}$, or other heteropoly acid can be added to the heated mixture followed by further heating until a polymer product is formed. The product can be collected in methanol, then refrigerated overnight. The polymer can be separated and dissolved in dimethylformamide (DMF) with addition of a few crystals of oxalic acid to facilitate dissolving to form a fourth mixture. A few drops of diluted $H_2SO_4$ can then be added to the fourth mixture. The fourth mixture can be spread over a flat support to form a membrane. The membrane can be dried, then heated at 80° C. for crosslinking. The membrane can then be used for separation in a pervaporation unit.

According to an embodiment, the membrane can be formed by dissolving about 4.5 grams of maleic anhydride in about 5 mL of acetone to form a first mixture. About 5 mL of styrene can then be added to the first mixture to form a second mixture. Then, about 5 mL of 2,3-dihydro-4H-pyran can be added to the second mixture to form a third mixture. The third mixture can be mixed to homogeneity by heating to about 60° C. Then, about 0.25 g of $H_3PW_{12}O_{40}$ (or any other heteropoly acid catalyst) can be added to the heated mixture. Heating can be continued at about 60° C. for about 2 hours until a product is formed. The product can be collected in methanol, then refrigerated overnight. The polymer can be separated and dissolved in Dimethylformamide (DMF) with addition of a few crystals of oxalic acid to facilitate dissolving. A few drops of diluted $H_2SO_4$ can then be added to the mixture and the mixture can be spread over a Teflon-plate surface to form a membrane. The membrane can be dried, then heated at 80° C. for cross-linking. The membrane can then be used for separation in a pervaporation unit.

The present method yields high quantities of cyclohexanone in an environmentally-friendly process. In addition, the cyclohexanone obtained using this process can have a high degree of purity. High purity of cyclohexanone is desirable when using cyclohexanone for other synthesis reactions, for example, polymerization of caprolactam. High purity of cyclohexanone can avoid coloration of the polyamide and provide aging resistance.

Figure 3:
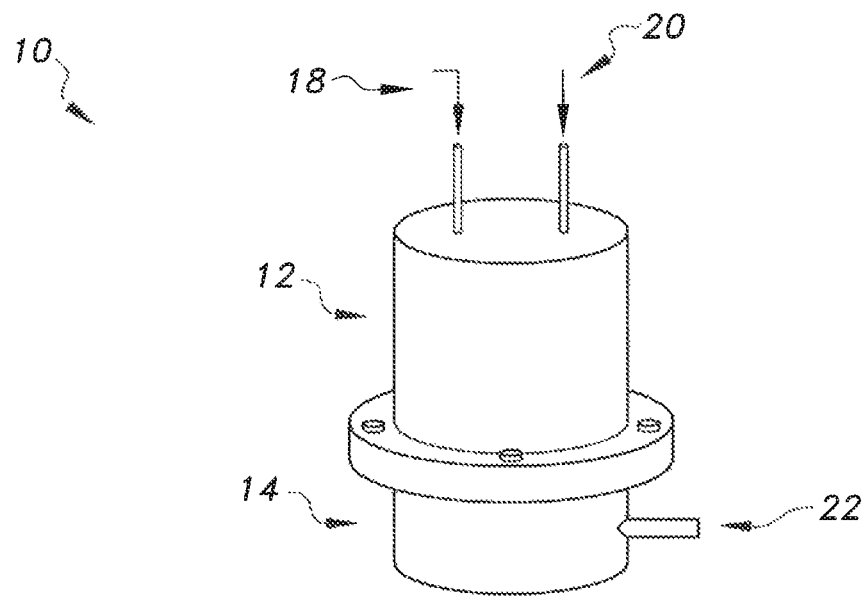
FIG. 3 depicts a diagram of a pervaporation cell.
Figure 4:
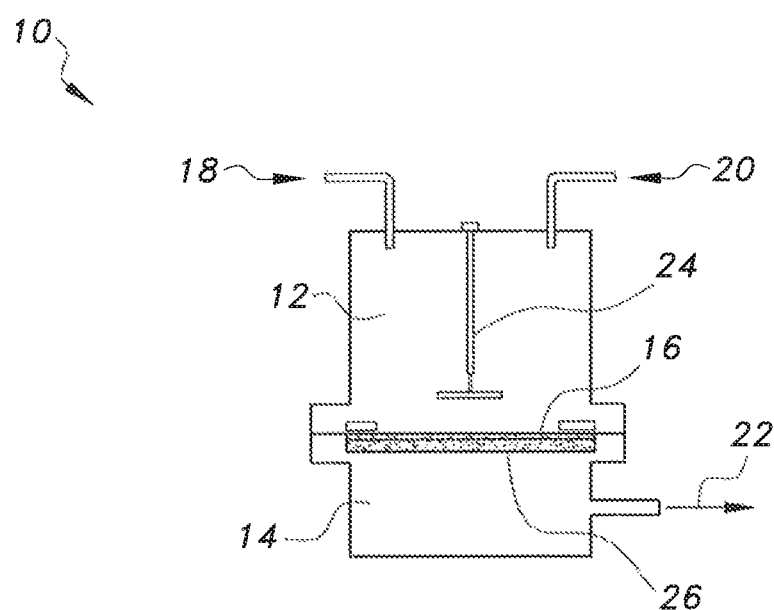
FIG. 4 depicts a cross-section of the cell shown in FIG. 3.

The pervaporation unit can include the poly(styrene-maleic anhydride-dihydropyrane) pervaporation membrane. As shown in FIGS. 3-4, the pervaporation unit 10 can be a hollow housing including an upper reactant-receiving portion 12, a lower permeate-receiving portion 14, and the poly(styrene-maleic anhydride-dihydropyrane) pervaporation membrane 16 extending across the unit and separating the reactant-receiving portion 12 from the permeate-receiving portion 14. The pervaporation membrane 16 can be positioned on a suitable horizontal support 26 such as a sintered stainless steel disk 26. The upper reactant-receiving portion 12 has a first opening for a first upper inlet port 18 and a second opening for a second upper inlet port 20. The first upper inlet port 18 is configured for receiving a cyclohexane feedstock therethrough. The second upper inlet port 20 is configured for receiving oxygen therethrough. The lower permeate-receiving portion 14 has an opening for a lower vacuum port 22. An overhead stirrer 24 extends into the reactant-receiving portion 12 for stirring the cyclohexane.

The following examples illustrate the present subject matter.

Example 1

Synthesis of Poly(Styrene-Maleic anhydride-Dihydropyrane) membrane

The poly(styrene-maleic anhydride-dihydropyrane) membrane was synthesized by cationic polymerization of a mixture of styrene, maleic and dihydropyrane monomers as described below. The polymerization was catalyzed by heteropoly acid catalysts under mild reaction conditions.

4.5 grams of maleic anhydride was dissolved in 5 mL of acetone to form a mixture. Then, 5 ml of styrene was added to the mixture, followed by addition of 5 ml of 2,3-dihydro-4H-pyran. This mixture was mixed to homogeneity by heating at 60° C. Then, 0.25 g of $H_3PW_2O_{40}$ (or any other heteropoly acid) catalyst was added to the heated mixture. Heating was continued at 60° C. for 2 hours until a product was formed. The product was collected in methanol, then refrigerated overnight. The polymer was separated and dissolved in Dimethylformamide (DMF) with addition of a few crystals of oxalic acid to facilitate dissolving. A few drops of diluted $H_2SO_4$ were then added to the mixture and the mixture was then spread over a Teflon-plate surface to form a membrane. The membrane was dried outside, then heated at 80° C. for crosslinking. The membrane was then ready for use in a pervaporation unit for separation in pervaporation experiments.

The membrane was used to separate a mixture of cyclohexane:cyclohexanone:cyclohexanol having a 3:1:1 ratio. The samples were passed through the membrane at set time intervals and collected in a tube cooled in liquid nitrogen under vacuum and with overhead stirring. The initial volume of the mixture was 20 mL for each test.

Analysis of the collected samples revealed that the membrane only separated cyclohexanone from the mixture.

Example 2

Pervaporation Procedure

Pervaporation of the cyclohexane-cyclohexanone-cyclohexanol mixture was carried out through the Poly(Styrene-Maleic anhydride-Dihydropyrane) pervaporation membrane by an ordinary pervaporation technique (FIG. 1). The membrane area was contacted with the feed solution. Details of the pervaporation cell are provided in FIGS. 3 and 4, respectively. The membrane was supported on a porous sintered stainless steel disk. Pervaporation was carried out at room temperature. The composition of permeate was determined with a gas chromatograph and it was found that it contained only cyclohexanone. Cyclohexane and cyclohexanol were rejected by the membrane.

The as-synthesized membrane showed high perm-selectivity toward cyclohexanone over the cyclohexane feed.

It is to be understood that the present synthesis method is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing cyclohexanone comprises:
   oxidation of cyclohexane to produce a mixture including cyclohexanone, cyclohexanol, and cyclohexane; and
   separating the cyclohexanone from the mixture by pervaporation using a pervaporation membrane of poly(styrene-maleic anhydride-dihydropyrane).

2. The method of claim 1, wherein the mixture is contacted with a first side of the pervaporation membrane and the cyclohexanone is received from a second side of the pervaporation membrane as a low pressure vapor.

3. The method of claim 1, wherein the pervaporation membrane is synthesized by cationic polymerization of a mixture of styrene monomers, maleic monomers, and dihydropyrane monomers.

4. The method of claim 1, wherein the oxidation occurs within a pervaporation cell, the pervaporation cell including the pervaporation membrane disposed on a porous horizontal support between a reactant receiving portion and a permeate receiving portion of the cell.

5. The method of claim 4, wherein separating the cyclohexanone from the mixture comprises dispensing the mixture into the reactant receiving portion of the pervaporation cell, supplying oxygen to the reactant receiving portion of the pervaporation cell, and passing the cyclohexanone through the membrane into the permeate receiving portion of the cell.

6. The method of claim 1, wherein the mixture comprises a cyclohexane:cyclohexanone:cyclohexanol ratio of 3:1:1.

7. The method of claim 1, wherein the pervaporation membrane is synthesized by:
   dissolving maleic anhydride in acetone to form a first mixture;
   adding styrene to the first mixture to form a second mixture;
   adding 2,3-dihydro-4H-pyran to the second mixture to form a third mixture;
   heating the third mixture until a product is formed;
   cooling the product;
   dissolving the product in dimethylformamide to form a fourth mixture; and
   heating the fourth mixture to form a membrane.

8. A method of synthesizing cyclohexanone comprises:
   oxidation of cyclohexane to produce a mixture including cyclohexanone, cyclohexanol, and cyclohexane; and
   separating the cyclohexanone from the mixture by contacting a first side of a pervaporation membrane with the mixture and receiving the cyclohexanone from a second side of the pervaporation membrane as a low pressure vapor,
   wherein the pervaporation membrane comprises poly(styrene-maleic anhydride-dihydropyrane).

9. A method of synthesizing a pervaporation membrane, comprising:
   dissolving maleic anhydride in acetone to form a first mixture;
   adding styrene to the first mixture to form a second mixture;
   adding 2,3-dihydro-4H-pyran to the second mixture to form a third mixture;
   heating the third mixture until a product is formed;
   cooling the product;
   dissolving the product in dimethylformamide to form a fourth mixture; and
   heating the fourth mixture to form the membrane.

10. The method of claim 9, wherein about 4.5 grams of maleic acid is dissolved in about 5 mL of acetone to form the first mixture, about 5 mL of styrene is added to the first mixture to form the second mixture, and about 5 mL of 2,3-dihydro-4H-pyran is added to the second mixture to form the third mixture.

11. The method of claim 10, wherein the fourth mixture is heated to a temperature of about 60° C.

12. A pervaporation membrane synthesized according to the method of claim 9.

* * * * *